US00PP11915P2

(12) United States Plant Patent
Bristo

(10) Patent No.: US PP11,915 P2
(45) Date of Patent: Jun. 12, 2001

(54) BERMUDAGRASS GRASS PLANT NAMED 'ADDIS'

(76) Inventor: Gene A. Bristo, 4204 Stamps Ave., Vernon, TX (US) 76384

( * ) Notice: Subject to any disclaimer, the term of this patent is extended or adjusted under 35 U.S.C. 154(b) by 0 days.

(21) Appl. No.: 09/253,430

(22) Filed: Feb. 18, 1999

(51) Int. Cl.[7] ..... A01H 5/00

(52) U.S. Cl. ..... Plt./389
(58) Field of Search ..... Plt./389

*Primary Examiner*—Bruce R. Campell
*Assistant Examiner*—Anne Marie Grünberg

(57) ABSTRACT

An asexually reproduced variety of perennial bermudagrass with a unique combination of characters including a chromosome number of 2N=4X=36, stolons with long internodes and large stem diameter, improved winterhardiness, and a distinct DNA fingerprint.

5 Drawing Sheets

The present invention relates to a new and distinctly asexually reproduced variety of bermudagrass (*Cynodon dactylon* (L.) Pers).

BRIEF SUMMARY OF THE INVENTION

Background of the Invention

This invention relates to a new and distinct perennial bermudagrass cultivar (*Cynodon dactylon*), tested under the designations "Addis" and "GB". I discoverd 'Addis' under cultivated conditions in a field near Vernon, Tex. 'Addis' was identified as a distinctly different vegetative patch or segregated clonal plant differing by improved winter hardiness from the variety 'Callie.' The grass identified as 'Addis' differed from 'Callie' in that after freezing temperatures, 'Addis' entered dormancy, and with the resumption of warm temperatures, resumed growth. Similar cold temperatures killed the surrounding 'Callie'. 'Callie' is not patented and was never a commercial success due to its lack of winter survival. I asexually reproduced 'Addis' by taking stolons of the plant material from the field, cutting the stolons and rhizomes into segments, each with a vegetative bud, and rooted them in potting media in a greenhouse in Vernon, Tex.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Bermuda grass plant named 'Addis'.

BRIEF DESCRIPTIONS OF THE ILLUSTRATIONS

FIG. 1 is a photograph of the leaf blade and ligule of 'Addis'.

FIG. 2 is a photograph of stigmas and anthers of 'Addis.'

FIG. 3 is a photograph of the stolon tip of 'Addis' and inflorescence of 'Addis.'

COMPLETE DESCRIPTION OF THE VARIETY

Figure 4:
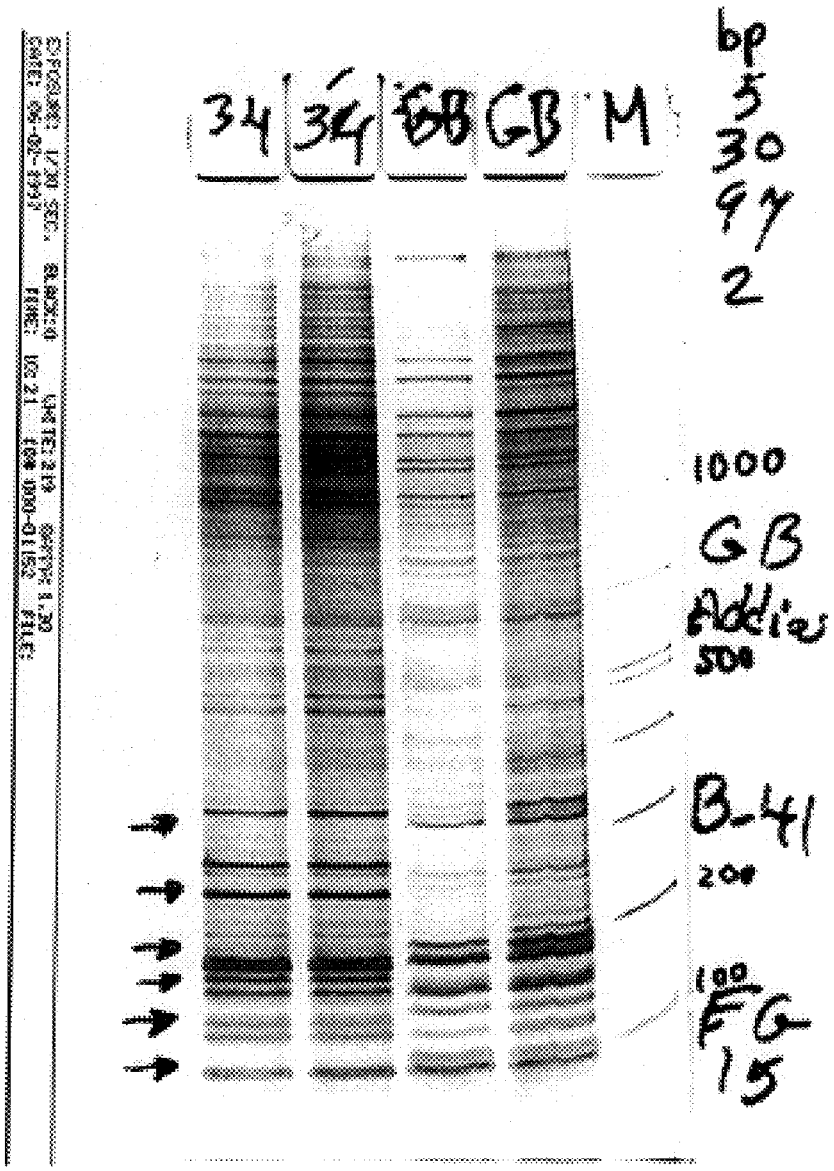
FIGS. 4 and 5 are the DNA fingerprints of 'Addis' in contrast with 'Tifway' (lane marked as 34).

'Addis' was characterized in greenhouse and field conditions. 'Addis' is a unique variety of bermudagrass (*Cynodon dactylon* (L.) Pers) that was discovered under cultivated conditions as superior in winter survival from the original, unpatented variety 'Callie'. Addis was propagated by me under greenhouse conditions at Vernon, Tex. by cutting of stolons and rhizomes, rooting them in soil, and planting of the rooted material to provide planting stock for studying performance and for comparison of morphological characters after propagation. 'Addis' has been propagated by stolons, rhizomes, sod, and sprigs. No seedling establishment from 'Addis' has been noticed in either greenhouse or field studies.

'Addis' spreads by both stolons and rhizomes, but the plant is most strongly stoloniferous and weakly rhizomatous. Characteristics of 'Addis' as follows were taken at time of first flowering in spring with a 14-hour daylength from greenhouse grown plants. The greenhouse was located near Albany, Oreg., with a nighttime temperature low of 65 degrees F., and a daytime high of 92 degrees F. The plants were held under natural daylight, supplemented with metal halide lights with photosynthetically active radiation equivalent to approximately 80% sunlight. The plants were fertilized with the equivalent of 1 pound of actual N per month, using a soluble fertilizer with an analysis of 20-20-20 in 4 equal soluble applications per month.

The stolons of 'Addis' are very large in length and diameter, with a mean internode length of 95.7 mm between the second and third nodes, with a mean stolon dimension or stem diameter of 2.11 mm×2.79 mm near and above the second youngest node; mean internode length between the third to fourth internode was 106.0 mm. The stolons of 'Addis' root adventitiously at the nodes. Color notations of plant tissues were based on the Munsell *Color Charts for Plant Tissues,* Munsell Color, Baltimore, Md., 1977. Light quality, photoperiod, and general growth of the plants affect color notations. The nodes of 'Addis' exposed to light exhibit a purplish red coloration, rated as 5 RP 4/10. The stolons and internodes of stolons exposed to light exhibit a green color, noted as 5 GY 7/6. The rhizomes are a whitish yellow in color, rated as 2.5 Y 8/2.

Leaf blades of 'Addis' are folded in the bud. The third youngest vegetative leaf blade ranges from 16.7 to 32.9 mm with a mean of 24.7 mm in length and a mean width of 3.9 mm. Leaf sheath length of the 3$^{rd}$ youngest vegetative leaf ranges from 32.4 to 61.4 mm, with a mean of 50.5 mm.

Measured under greenhoue conditions in January 1996, the genetic, adxial leaf color of 'Addis' is 7.5 GY 5/4. The ligule of 'Addis' is a membranous fringe with silky hairs, approximately 2.9 mm in length for the longest hairs. 'Addis' is lacking in auricles, and has a mean flag leaf length of 26.3 mm. 'Addis' has white anthers tinged with purple (tinge rated as 5 RP 3/8) and purple colored stigmas, rated as 5 RP 3/8. Pollen is present and is whitish yellow in color, rated as 2.5 Y 8/2. The inflorescence of 'Addis', many in number, is a panicle of usually 4–6 digitately (up to 9) arranged spicate branches. The panicle branches of 'Addis' have a mean length of 77.0 mm. When 'Addis' is unmown, the approximate total plant height is 35.6 cm.

Measured from field grown plants, the spikelet length is 2.5 mm long, with glumes 1.5 mm in length.

The chromosome complement of 'Addis' is 2N=4X=36. The seed fertility level of Addis is 0, with no seed set noted. The variety 'Callie' is noted to have as much as 5% seed fertility.

In forage analysis tests conducted by a private laboratory, 'Addis' showed a crude protein of 13.94%, digestible protein of 8.87%, acid detergent fiber of 40.05%, total digestible nutrients of 57.75%, and nitrogen of 2.23%, all based on zero or Moisture Free basis. The protein analysis was conducted on Jul. 30, 1997, at full flowering but without any seed production, on hay produced near Vernon, Tex. on non-irrigated sandy soils. Prior to the protein analysis, 'Addis' was fertilized on approximately March 15 with 200 pounds per acre of 25-15-0-12 (N.P.K.S) fertilizer. 'Addis', in an approximately 90% pure stand, produced approximately 3000 pounds per acre of dry foliage. 'Addis' has shown no susceptibility to disease, and is very vigorous in vegetative growth.

'Addis' survived low winter temperatures of less than 20 degrees F. at Vernon, Tex. over 29 separate days during the winter of 1995–96.

DETAILED SUMMARY OF DNA FINGERPRINT ANALYSIS

See "Caetano-Anolles, G., Callahan, L. M. and Gresshoff, P. M. (1997) Inferring the origin of bermudagrass (Cynodon) off-types by DNA amplification fingerprinting in phytoforensic applications. Crop Science 37: 81–87.

See "Caetano-Anolles, G., Callahan, L. M., Williams, P. E., Weaver, K. and Gresshoff, P. M. (1995) DNA amplification fingerprinting analysis of bermudagrass (Cynodon): genetic relationships between species and interspecific crosses. Theor. Appl. Genetics 91: 554–559.

See "Weaver, K., Callahan, L. M., Caetano-Anolles, G. and Gressshoff, P. M. (1995) DNA amplification fingerprinting and hybridization analysis of centipedegrass. Crop Science 35: 881–885.

Figure 5:
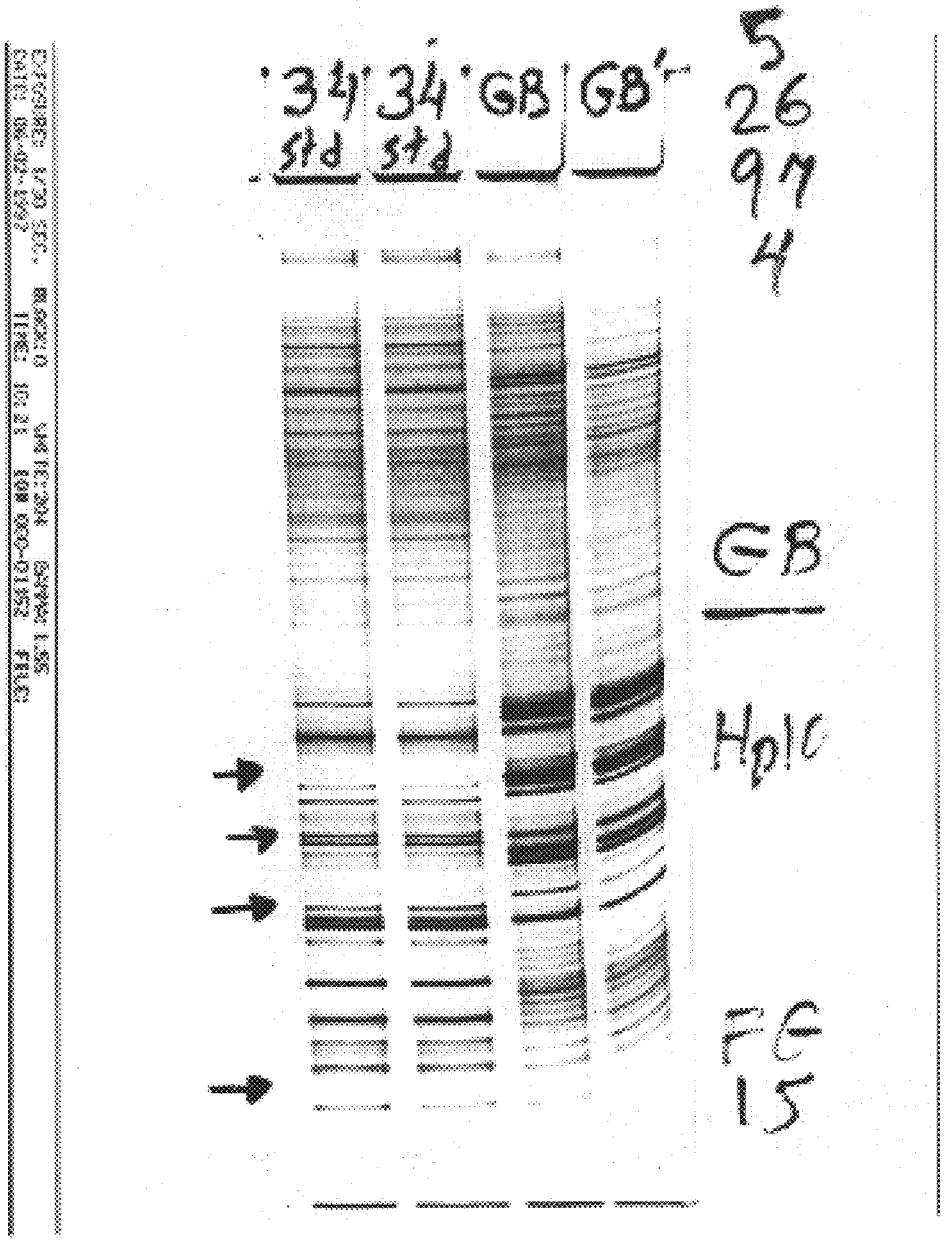

Dr. Peter Gresshoff of the University of Tennessee provided the DNA analysis. The amplification profiles of 'Addis' (FIG. 4, identified as 'GB') were obtained using DAF and primer OcB41, and are compared to the standards 'Tifway 419' (identified as #34). The amplification profiles of 'Addis' (FIG. 5, identified as 'GB') were obained using DAF and primer Hp10, and are compared to the standards 'Tifway 419' (identified as #34). Complex banding patterns and amplification fragment length polymorphisms were obtained in all cases. Results indicate bands fall into two categories, those that are common to the varieties, and those that in combination are characteristic of the cultivar (some identified by arrows). 'Addis' may be distinguished from 'Tifway 419' based upon its amplification profile.

I claim:

1. A new and distinct variety of bermudagrass plant, substantially as described and illustrated herein, characterized particularly by having a chromosome complement of 2N=4X=36, and other principle distinguishing characteristics of long stolons with long internodes and large stem diameter, improved winterhardiness, and a distinct DNA fingerprint.

* * * * *